(12) United States Patent
Bourne et al.

(10) Patent No.: US 10,228,436 B2
(45) Date of Patent: Mar. 12, 2019

(54) PHANTOMS AND ASSOCIATED METHODS FOR CALIBRATING IMAGING SYSTEMS

(71) Applicant: Elekta Limited, West Sussex (GB)

(72) Inventors: Duncan Bourne, Surrey (GB); Martin Sell, Horley (GB)

(73) Assignee: Elekta Limited, West Sussex (GB)

( * ) Notice: Subject to any disclaimer, the term of this patent is extended or adjusted under 35 U.S.C. 154(b) by 0 days.

(21) Appl. No.: 15/663,191

(22) Filed: Jul. 28, 2017

(65) Prior Publication Data

US 2018/0024218 A1    Jan. 25, 2018

Related U.S. Application Data

(63) Continuation of application No. 14/524,255, filed on Oct. 27, 2014, now Pat. No. 9,726,745.

(30) Foreign Application Priority Data

Oct. 28, 2013  (GB) .................................. 1318958.4

(51) Int. Cl.
  *G01R 33/58*  (2006.01)
  *A61B 6/00*   (2006.01)
  (Continued)

(52) U.S. Cl.
  CPC .............. *G01R 33/58* (2013.01); *A61B 5/055* (2013.01); *A61B 6/5235* (2013.01); *A61B 6/583* (2013.01);
  (Continued)

(58) Field of Classification Search
  CPC ....... G01R 33/58; A61B 6/584; A61B 6/5235; A61B 6/583; A61B 6/032; A61B 5/0037;
  (Continued)

(56) References Cited

U.S. PATENT DOCUMENTS 3,888,111 A   6/1975 Craig
4,173,139 A   11/1979 Conn
(Continued)

FOREIGN PATENT DOCUMENTS

EP    1414004 B1    4/2004
EP    2267484 A1    12/2010
(Continued)

OTHER PUBLICATIONS

Rhod et al.; "Registration and Tracking to Integrate X-Ray and MR Images in an XMR Facility"; IEEE Transactions on Medical Imaging; vol. 22; pp. 1369-1378; Nov. 2003.
(Continued)

*Primary Examiner* — Daniel S Larkin
(74) *Attorney, Agent, or Firm* — Finnegan, Henderson, Farabow, Garrett & Dunner LLP (57) ABSTRACT

Embodiments of the present invention provide phantoms, and associated methods of calibration which are suitable for use in both medical resonance imaging and radiographic imaging systems. A phantom for calibration of a medical imaging system, comprises a first component having a first outer shape, a portion of which defines part of at least one pocket; and a second component coupled to the first component and having a second outer shape, a portion of which defines another part of the at least one pocket. At least one of the first and second components comprises a reservoir, the reservoir having a shape at least a portion of which locates a center of the at least one pocket.

18 Claims, 4 Drawing Sheets

(51) Int. Cl.
*A61N 5/10* (2006.01)
*A61B 5/055* (2006.01)
*A61B 6/03* (2006.01)
*A61B 5/00* (2006.01)

(52) U.S. Cl.
CPC .......... *A61N 5/1075* (2013.01); *A61B 5/0037* (2013.01); *A61B 6/032* (2013.01); *A61B 6/584* (2013.01); *A61B 2560/0223* (2013.01); *A61N 5/1081* (2013.01); *A61N 2005/1054* (2013.01); *A61N 2005/1055* (2013.01); *A61N 2005/1076* (2013.01)

(58) Field of Classification Search
CPC ............ A61B 5/055; A61B 2560/0223; A61N 5/1075; A61N 5/1081; A61N 2005/1076; A61N 205/1054; A61N 2005/1055
USPC .................................................. 73/1.86, 49.3

See application file for complete search history.

(56) References Cited

U.S. PATENT DOCUMENTS

| | | |
|---|---|---|
| 4,357,222 A | 11/1982 | Lucek |
| 5,275,546 A | 1/1994 | Fierkens |
| 6,354,142 B1 | 3/2002 | Nothhelfer et al. |
| 6,992,280 B2 | 1/2006 | White et al. |
| 2007/0210796 A1 | 9/2007 | Woo et al. |
| 2009/0190723 A1 | 7/2009 | Jang et al. |
| 2009/0213995 A1 | 8/2009 | Levine et al. |

FOREIGN PATENT DOCUMENTS

| | | |
|---|---|---|
| GB | 2504258 A | 1/2014 |
| JP | S60-207655 | 10/1985 |
| JP | H07-327971 | 12/1995 |
| JP | 2009195614 A | 9/2009 |
| WO | 2011127947 A1 | 10/2011 |

OTHER PUBLICATIONS

Office Action dated Jun. 18, 2018, issued by the Japanese Patent Office in corresponding Japanese Patent Application No. 2014-218065 (3 pages).

PHANTOMS AND ASSOCIATED METHODS FOR CALIBRATING IMAGING SYSTEMS

CROSS-REFERENCE TO RELATED PATENT APPLICATION

This application is a continuation of application Ser. No. 14/524,255, filed Oct. 27, 2014, now U.S. Pat. No. 9,726,745, which claims priority under 35 U.S.C. § 119 to United Kingdom Patent Application No. 1318958.4, filed Oct. 28, 2013, the entire contents of the above-identified applications are incorporated herein by reference.

TECHNICAL FIELD

The present invention relates to medical imaging, and particularly to phantoms and associated methods of calibrating an imaging system which may be integrated with a radiotherapy system.

BACKGROUND

Recent developments in the field of radiotherapy have focussed on integrating an imaging system with the therapeutic system. The goal is to provide real-time feedback on the location of an anatomical feature within the patient (e.g. a tumour) such that a therapeutic radiation beam can be more accurately controlled to target that feature, One suggested approach is to combine a linear accelerator-based therapeutic system with a magnetic resonance imaging (MRI) system within a single apparatus, known as an MRI-Linac. Such apparatus is described in a number of earlier applications by the present Applicant, including U.S. patent application Ser. No. 12/704,944 (Publication No. 2011/0201918) and PCT Publication No. 2011/127947. In the system described in each of these earlier applications, the magnetic coils of the MRI system are split, leaving a gap through which a therapeutic radiation beam can be delivered to the patient. In this way, the patient can be imaged and treated substantially simultaneously while lying in the same position.

If the MRI system is to provide reliable information to the therapeutic system, it is important that the two systems are accurately calibrated; that is, the coordinate system of the MRI system must be registered to that of the treatment beam so that measurements in the MRI system can be translated into instructions in the therapy system.

Phantoms are known devices which are scanned or imaged to evaluate and tune the performance of various medical imaging devices. A paper by Rhode et al ("Registration and Tracking to Integrate X-Ray and MR Images in an XMR Facility", IEEE Transactions on Medical Imaging, Vol. 22, pages 1369-1378) describes a method of registering x-ray and MR images in which a phantom is first imaged in an x-ray system before being translated a distance and imaged by an MRI system. The distance between the two systems is measured to enable the two coordinate systems to be co-registered. When in the x-ray system, ball bearings are used as markers within the phantom; when in the MRI system, the ball bearings are replaced by MR imaging markers to avoid problems arising from interactions with the intense magnetic field. This system has several drawbacks. The replacement of the ball bearings with MR imaging markers introduces a potential source of error if the two markers are not exactly co-located within the phantom. In addition, the translation of the phantom between the two devices introduces a further source of error.

SUMMARY OF INVENTION

According to a first aspect of the present invention, there is provided a phantom for calibration of a medical imaging system, comprising: a first component having a first outer shape, a portion of which defines part of at least one pocket; and a second component coupled to the first component and having a second outer shape, a portion of which defines another part of the at least one pocket. At least one of the first and second components comprises a reservoir, the reservoir having a shape at least a portion of which locates a centre of the at least one pocket.

BRIEF DESCRIPTION OF THE DRAWINGS

For a better understanding of the present invention, and to show more clearly how it may be carried into effect, reference will now be made, by way of example, to the following drawings, in which.

DETAILED DESCRIPTION

Figure 1:
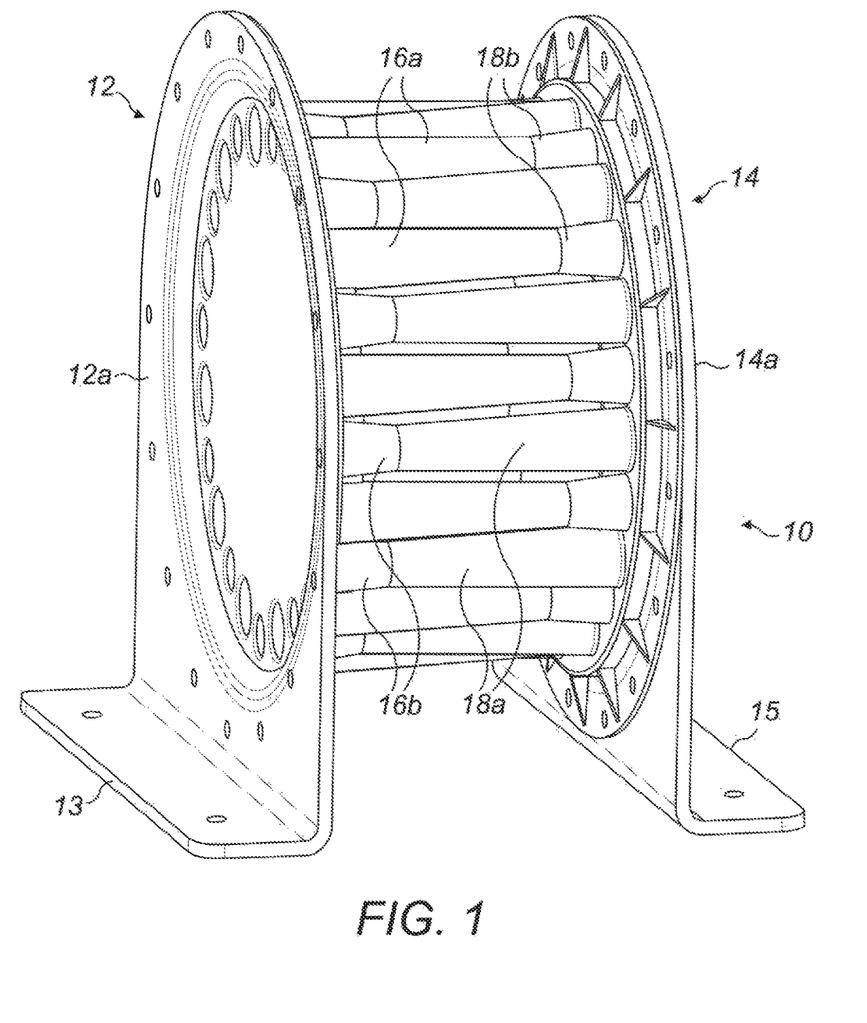
FIG. 1 shows a phantom according to embodiments of the present invention.

FIG. 1 shows a phantom 10 according to embodiments of the present invention. As will be explained below, the phantom 10 is suitable for use in a variety of medical imaging systems using different imaging modalities.

In order to understand how the marker works, it is instructive first to consider the different imaging mechanisms which may be employed in medical imaging.

Magnetic resonance (MR) imaging operates by placing the imaging object in a high strength magnetic field. Currently, the field strength density typically varies from system to system between 0.2 and 3 T. In this strong magnetic field, the magnetic moments of hydrogen protons in the object become aligned with the magnetic field. By applying an electromagnetic signal having a resonant frequency to the object, the spins of those protons can be made to flip. When the electromagnetic signal is switched off, the protons flip back and emit an electromagnetic signal which can be received in receiver coils. Gradient magnets are employed to vary the magnetic field spatially, so as to generate detectable signals only from certain locations within the object and/or to make the resonant frequency differ at different locations to enable spatial encoding of received electromagnetic signals. Hydrogen protons in different materials return to their equilibrium state at different relaxation rates, and this can also be used to differentiate between materials and construct images.

In this way, materials with high hydrogen proton densities, i.e. materials with high numbers of hydrogen protons which are free to flip their magnetic moment, are clearly and strongly visible in MR images.

Another imaging modality employs radiation such as x-rays. An object to be imaged is targeted with a collimated x-ray beam; typically the beam is cone-shaped, but other shapes could be employed. A detector positioned on the opposite side of the body detects the radiation after it has passed through the object. Some of the radiation will have been absorbed by the object, such that the data collected by the detector provides information on the location of the object in the form of a projection image. Multiple projection images can be combined to reconstruct a volume image of the object using computed tomography (CT) techniques.

The likelihood of an object absorbing x-rays of a given energy increases with increasing material density of the object, although the increase is not linear. High-density materials such as lead or tungsten absorb x-rays very readily, which leads to them being employed in collimators, radiation shields and the like. Low-density objects may not be visible in radiation-based images. The likelihood of absorption also depends on the energy of the radiation, with different mechanisms of interaction dominating at different energies. For example, in the case of lower energy x-rays (i.e. keV range), in addition to the effects of material density, x-ray absorption can be quite material sensitive due to the photoelectric effect. Different materials absorb keV x-rays differently (e.g. as seen in the clear imaging of bone in keV x-rays). However, at higher energy levels (i.e. MeV range) the relative absorption depends mainly on the relative material density of the materials in the object. At MeV energy levels, therefore, a high contrast image can be obtained by imaging materials with different material densities. The greater the difference in material density, the greater the contrast in the image.

The phantom 10 according to embodiments of the present invention can be employed in imaging systems employing these and other techniques.

The phantom 10 comprises two components 12, 14. In the illustrated embodiment, these two components comprise similar features and have complementary shapes.

The first component 12 comprises an upstanding, substantially planar support 12a, with a flange 13 extending from the base of the support 12a to allow the first component 12 to remain upright during use. A plurality of elongate members extend in a direction out of the plane of the support 12a. In the illustrated embodiment, the elongate members comprise relatively long members 16a and relatively short members 16b, and these are arranged in a ring. The relatively long members 16a alternate with the relatively short members 16b in a circumferential direction around the ring. In the illustrated embodiment, each elongate member (i.e. both long 16a and short 16b) is tapered towards the end furthest from the support 12a.

The second component 14 similarly comprises an upstanding, substantially planar support 14a, with a flange 15 extending from the base to allow the second component 14 to remain upright during use. A plurality of elongate members extend in a direction out of the plane of the support 14a and, in the illustrated embodiment, the elongate members again comprise relatively long members 18a and relatively short members 18b. The elongate members 18a, 18b are arranged in a ring. The relatively long members 16a alternate with the relatively short members 16b in a circumferential direction around the ring.

In the illustrated embodiment, each elongate member (i.e. both long 18a and short 18b) is tapered towards the end furthest from the support 14a.

The first and second components 12, 14 are coupled together such that the relatively long members 16a of the first component 12 engage with the relatively short members 18b of the second component 14, while the relatively short members 16b of the first component 12 engage with the relatively long members 18a of the second component 14. In this way, the points of engagement between the two components 12, 14 form two rings: one ring formed near the support 12a by the points of engagement between the relatively long members 16a of the first component 12 and the relatively short members 18b of the second component 14; and a second ring formed near the support 14a by the points of engagement between the relatively short members 16b of the first component 12 and the relatively long members 18a of the second component 14.

In the light of the description below, it will be apparent to those skilled in the art that alternative dimensions may be chosen for the elongate members without departing from the scope of the invention, as long as each elongate member of one component engages with a corresponding member of the other component. For example, the elongate members of the components may all have the same length such that a single ring of points of engagement is created. Alternatively, the elongate members may all have different lengths such that a different pattern is created; for example, the points of engagement may follow a spiral shape.

Any suitable mechanism may be employed to join the elongate members 16a, 16b, 18a, 18b and, more generally, the first and second components together. For example, the respective pairs of members 16a, 18b and 16b, 18a may be joined together by an adhesive at their point of engagement. Alternatively, mechanical means (not illustrated) may be provided to couple the first and second components 12, 14 together. Those skilled in the art will appreciate that any suitable mechanism may be provided.

In some embodiments of the invention, both components 12, 14 are made from a non-conductive (i.e. non electrically conducting) and non-magnetic material. The material is non-magnetic, in that it has no significant effect on an external magnetic field (i.e. it is non-ferromagnetic). It is this feature which allows the phantom 10 to be employed in magnetic resonance (MR) imaging systems should that be required. Further, the material is non-conductive, as conductive materials can cause distortion in MR images.

In the context of the present invention, a component can be deemed non-conductive if the radio frequency field generated by an MRI system can penetrate (i.e. pass through) the component. The skin depth of the component material at such frequencies must therefore be substantially equal to or greater than the size of the component itself (the skin depth $\delta$ is given by $$\delta = \sqrt{\frac{2\rho}{\omega\mu}},$$

where $\rho$ is the resistivity, $\omega$ is the angular frequency and $\mu$ is the absolute magnetic permeability). For example, in a 1.5 T MRI the rf field frequency (the resonant frequency of hydrogen protons) will be at or around 64 MHz. Given this information, it is a simple exercise for the skilled person to select a suitable material to ensure that the skin depth is equal to or greater than the size of the component.

In one embodiment, the components 12, 14 are manufactured from moulded plastic. The phantom may be provided in a kit of parts, comprising the first and second components 12, 14.

Figure 2:
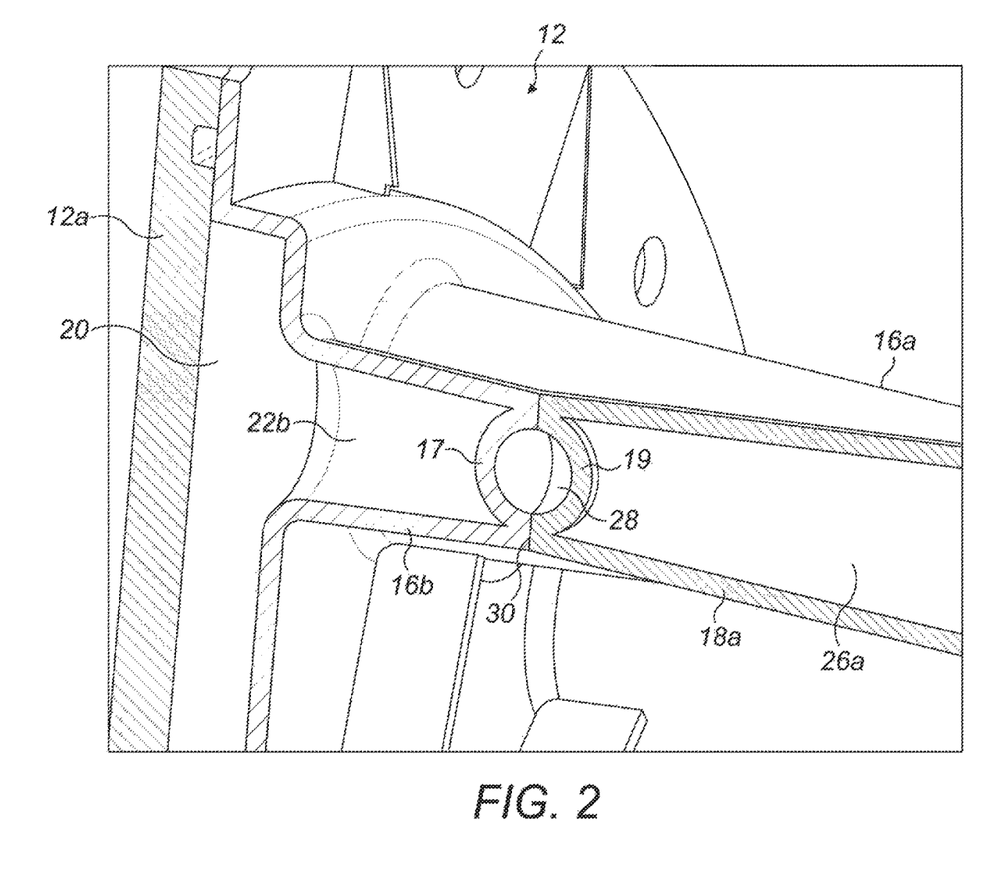
FIG. 2 shows in more detail a cross-section of the phantom illustrated in FIG. 1.

FIG. 2 shows a cross-section through part of the phantom 10 illustrated in FIG. 1, specifically through a relatively short member 16b of the first component 12 and a relatively long member 18a of the second component 14. Those skilled in the art that features illustrated in the cross-section are common to all members regardless of their length.

The short member 16b is shaped so as to taper towards the end furthest from the support 12a. At that end, the member is shaped to provide a concave section 17. The long member 18a is similarly tapered towards the end furthest from the support 14a, and similarly has a concave section 19 at that end. In use, the two ends of the members 16b, 18a are joined together along an intersection 30, and may be fixed using an adhesive, or through pressure applied by some mechanical means forcing the first and second components 12, 14 together. The combination of the two concave sections provides a volume, or pocket 28, between the two elongate members 16b, 18a. In some embodiments, the concave sections 17, 19 may each be hemispherical such that the pocket 28 is spherical. However, other shapes may be employed by those skilled in the art without departing from the scope of the invention. For simplicity, the concave sections of the two members 16b, 18a may have the same shape, but this is not essential.

In use, and prior to the two components 12, 14 being fitted together, a marker (not illustrated) can be placed in the or each pocket 28 of the phantom 10. The marker should be shaped so as to fit tightly within the pocket 28. In the illustrated embodiment, therefore, the marker would be spherical.

In one embodiment, the marker has a relatively high material density such that it preferentially absorbs x-rays and appears in radiation-based images, i.e. radiographic images using x-rays. For example, the marker may be manufactured from metal, such as ball bearing.

According to some embodiments of the invention, however, the phantom 10 should be able to be employed in a diverse range of systems, such as those which employ magnetic resonance imaging (MRI) techniques. In that case, a metal marker would be inappropriate owing to the high magnetic fields generated in such systems. One class of material which may be suitable for use as the marker in such situations is ceramics, as they are non-magnetic and non-conductive. Certain ceramic materials also have a high material density, such as zirconium oxide (zirconia) which has a material density of $5.66\ \text{kgm}^{-3}$. Those materials could be imaged by x-ray based imaging modalities without adversely affecting MRI-based methods. Thus in one embodiment the marker may be made of a ceramic, such as zirconia.

Ceramic materials also have a relatively low hydrogen proton density, however, so that they appear only weakly in MR images. In some embodiments, the marker may have substantially zero hydrogen proton density so that it is not imaged in MR imaging systems.

The first component 12 further comprises a hollow chamber, or reservoir 20, suitable for holding a liquid. The reservoir 20 is provided within the support 12a, but also extends into a hollow space 22b within the elongate member 16b. At the end of the member 16b, the reservoir is shaped in a similar manner to the concave section 17. That is, where the end of the member 16b comprises a concave section, the reservoir similarly has a concave section. In the illustrated embodiment, where the concave section 17 defines a portion of a spherical surface, the end of the reservoir similarly defines a portion of a spherical surface. Moreover, the locus of the spherical surface of the reservoir 20 is the same as the locus of the concave section 17.

In an embodiment, each of the elongate members 16a, 16b is hollow, with the hollow sections being connected as part of the reservoir 20.

In use, the reservoir 20 is filled with a liquid. The liquid may comprise an oil, such as cod liver oil. In alternative embodiments the liquid may comprise water or a water-based solution. Owing to its high hydrogen proton density, the liquid is easily imaged using MRI techniques. An MRI image of the phantom 10 therefore would show the liquid, which conforms to the shape of the reservoir 20. The concave shape of the liquid at the end of the reservoir, within the member 16b, can be used to determine the centre of the pocket 28.

In the illustrated embodiment, the elongate member 18a of the second component 14 is similarly hollow, comprising a hollow space 26a which has a concave, spherical shape towards the end furthest from the support 14a. Although not illustrated in FIG. 2, in embodiments the second component 14 also comprises a reservoir which is coupled to the hollow space 26a within the elongate member 18a. In further embodiments, the reservoir may be connected to all elongate members 18a, 18b of the second component 14 in a similar fashion.

In use, the reservoir within the second component 14 may also be filled with liquid and, when the phantom is imaged using MRI techniques, the combination of the liquid in the hollow space 22b and the liquid in the hollow space 26a allows the centre of the pocket 28 to be located with a high level of accuracy.

Figure 3:
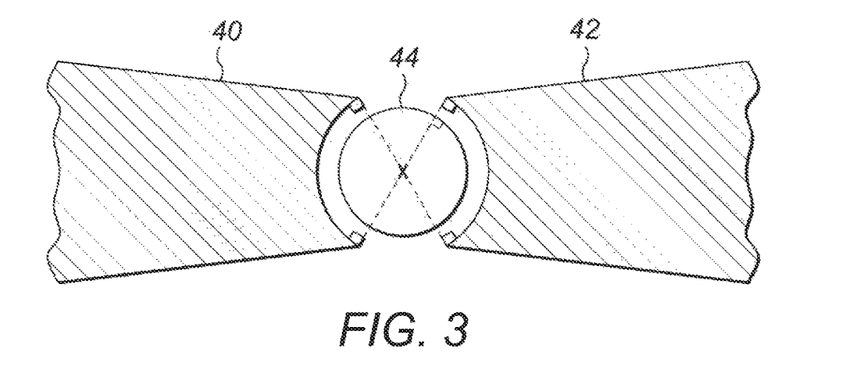
FIG. 3 is a schematic drawing showing how the phantom may be imaged.

Those skilled in the art will appreciate that alternative reservoir shapes than the partial spherical shapes illustrated may be employed which nonetheless locate the centre of the pocket 28. For example, the reservoir(s) may taper to a point at the end of the elongate members, thus providing an "arrow" which points to the centre of the pocket 28. The reservoir(s) may have a cuboid shape within the elongate members, the centre of which identifies the centre of the pocket 28. Alternative shapes will be apparent to the skilled person and all such shapes fall within the scope of the present invention. FIG. 3 is a schematic drawing illustrating how the phantom 10 can be imaged using various imaging modalities. Only the imaging of one pair of elongate members is shown for clarity. Liquid in each of the elongate members is shown by the shapes 40, 42. A marker placed in the pocket 28 is shown by the region 44.

In MR images, the liquid in the reservoirs is clearly visible, while the marker 44 may be dimly visible or completely invisible according to the hydrogen proton density. Nonetheless, the centre of the pocket (marked X) may be determined by analysing the location and shape of the liquid 40, 42 present in the images. In radiographic images, the converse is true. The liquid 40, 42 in the reservoirs may be only dimly visible or completely invisible due to the liquid's low material density. In contrast the marker region 44 will be clearly visible due to the high material density of the marker. The centre of the pocket 28 (X) can be determined by determining the centre of the marker region 44.

Note that the appearance of the liquid and marker regions in the radiographic image depends on a number of factors, including the energy of the radiation and the quantity of the radiation (i.e. as determined by the intensity of the beam and the exposure time). A small amount of radiation may result in the liquid effectively being invisible in the radiographic image.

The phantom 10 according to embodiments of the invention can therefore be employed to calibrate MRI systems (with or without markers in the pockets) and x-ray based imaging systems (with or without liquid in the reservoirs). In addition, the same point (or set of points)—the centres of the pocket(s)—is determined using magnetic resonance and radiographic techniques. This allows the marker to be employed in imaging systems using both modalities.

The phantom 10 thus has particular utility within MRI-Linac systems, which combine both magnetic resonance imaging and radiotherapy within the same system. Such a system 100 is shown schematically in FIG. 4.

Figure 4:
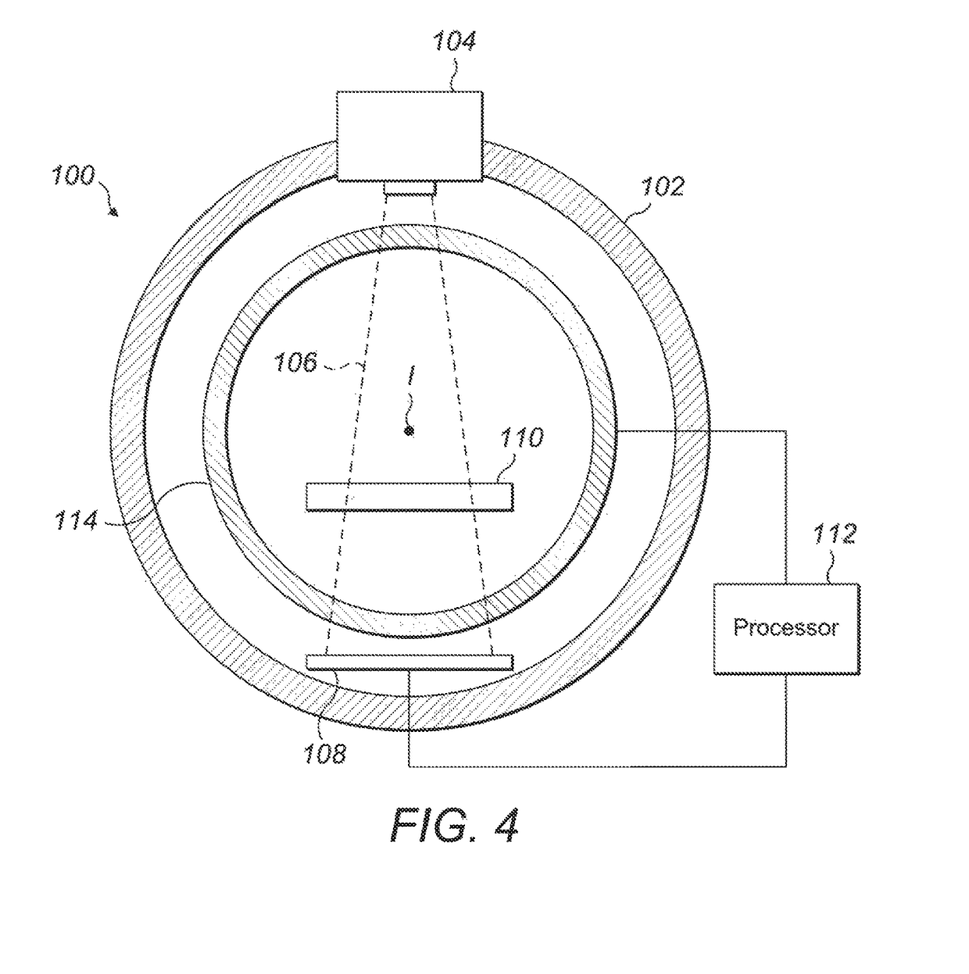
FIG. 4 shows a combined MRI radiotherapy system.

The system comprises a gantry 102, which is able to rotate about an axis I. A radiation head 104 is mounted to the gantry, and adapted to generate a beam of radiation 106 directed substantially inwards towards the rotation axis I. A source of radiation (such as a linear accelerator or a radio-isotope) may be provided to generate the radiation which emanates from the head 104. In order to have a therapeutic effect, the energy of the radiation beam will typically be in the order of megaelectronvolts. A patient support 110 is provided on or near the rotation axis I, on which a patient or an object to be imaged can be placed.

The shape and direction of the beam 106 can be adapted by the use of collimators such as a multi-leaf collimator (not illustrated), to conform to a particular desired profile. For example, the shape of the beam may be adapted to conform to the profile of a target structure within a patient on the patient support 110. As the gantry rotates, the radiation beam 106 is directed towards the target structure from multiple directions and dose builds up in the target structure while being generally reduced in the surrounding areas. A radiation detector 108 is mounted on the gantry 102 at a position substantially opposite the radiation head 104, such that the radiation beam 106 impacts the radiation detector 108 after passing through an object to be imaged on the patient support 110. Such detectors are often called portal imagers as they generate a projection image of the object along the axis of the radiation beam 106. The detector 108 is coupled to processing circuitry 112 which uses the detection data to produce an image. Thus, although the radiation system is primarily used for therapeutic purposes and generates radiation at an energy suitable for therapy, the radiation can nonetheless be used to generate images (albeit at lower contrast than the less energetic radiation conventionally used for imaging).

The system 100 further comprises a magnetic resonance imaging apparatus. Those skilled in the art will appreciate that such an apparatus comprises a large number of components, including various magnetic coils for generating specific magnetic field strengths at specific locations and an RF system for transmitting and receiving electromagnetic waves. Only the magnetic coils 114 are illustrated here for clarity. The magnetic coils 114 are positioned with their longitudinal axes aligned with the rotational axis I of the gantry 102. In one embodiment, the coils 114 are displaced from each other along the direction of the axis I such that a gap is created. The radiation beam 106 can be directed through this gap such that the magnetic coils 114 do not interfere with the radiation. The coils 114 are coupled to the processing circuitry 112 such that an image can be produced of an object on the patient support 110.

An object which is placed on the patient support 110 can therefore be imaged by the MRI system and treated by the radiotherapy system while in the same position. Further, the radiotherapy system can be used to generate a portal image of the object using the radiation detector 108. The phantom 10 described above can be used to calibrate the system 100 such that imaging data collected by the MRI system can be used to inform and control the radiotherapy system.

Figure 5:
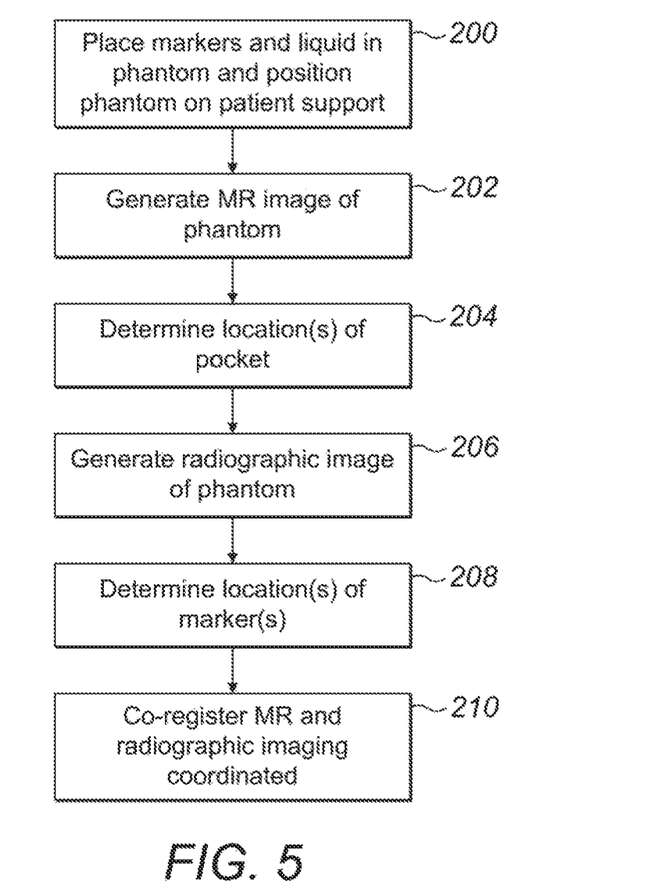
FIG. 5 is a flowchart of a method according to embodiments of the present invention.

FIG. 5 is a flowchart describing a method of calibrating the system 100 described above.

In step 200, one or more markers are placed within the one or more pockets 28 of a phantom 10 according to embodiments of the invention. The markers will be non-magnetic and non-conducting. The markers may be made from ceramic material such as zirconia. In some embodiments, the marker may be made of more than one material. That is, the marker may comprise a high-density material (e.g. zirconia) at its core, and a lower density material surrounding the core. It may be desirable for the high-density core to be as small as possible so as to maximise the accuracy of calibration of a radiation-based device, whilst maintaining a relatively large non-magnetic volume so as to preserve the accuracy of calibration of an MRI device. Liquid is placed within the one or more reservoirs, and the phantom is placed on the patient support 110, in the path of the radiation beam 106 and at a position suitable for imaging by the MRI system.

In step 202, the MRI system is used to generate an image of the phantom, and particularly used to generate an image showing the liquid in the reservoir(s).

In step 204, the locations of the centres of the one or more pockets are determined from the MRI image.

In step 206, a radiographic image is generated of the phantom using the radiation beam 106 and the radiation detector 108 while in the same position. In this image, the one or more markers show more clearly due to their higher material density.

In step 208, the locations of the centres of the one or more markers (and thus the centres of the pockets 28) are determined from the radiographic image.

In step 210, the knowledge of the locations of the centres of the one or more pockets 28 in both images allows the coordinate systems of the MR imaging modality to be co-registered with the coordinate system of the radiographic modality. In particular, measurements using the MRI system can be used to instruct the radiotherapeutic system. For example, the positions of the collimating elements may be adapted on the basis of MR imaging data in order to track a moving target.

It will be apparent to those skilled in the art that these steps need not be carried out strictly in the order specified for the method to be successfully carried out. For example, the radiographic image may be acquired before the MRI image without affecting the method, or both images may be acquired before either is analysed to determine the locations of the centres of the markers/pockets.

Embodiments of the present invention therefore provide phantoms and associated methods of calibration which are suitable for use in a wide variety of medical imaging systems.

Those skilled in the art will appreciate that various amendments and alterations can be made to the embodiments described above without departing from the scope of the invention as defined in the claims appended hereto.

The invention claimed is:

1. A phantom for calibration of a medical imaging system, comprising:
   a first component having a first outer shape, a portion of which defines part of at least one pocket; and
   a second component coupled to the first component and having a second outer shape, a portion of which defines another part of the at least one pocket;
   wherein at least one of the first or second component comprises a reservoir, the reservoir having a shape at least a portion of which locates a center of the at least one pocket.

2. The phantom of claim 1, wherein the portion of the shape of the reservoir conforms to a shape of the corresponding part of the at least one pocket.

3. The phantom of claim 1, wherein the portion of the shape of the reservoir conforms to a corresponding surface of the portion of the first or second outer shape defining the corresponding part of the at least one pocket.

4. The phantom of claim 1, wherein the portion of the second outer shape defines a remainder of the at least one pocket.

5. The phantom of claim 1, wherein the at least one pocket is spherical.

6. The phantom of claim 5, wherein the portions of the first and second outer shapes are each hemispherical.

7. The phantom of claim 5, wherein the portion of the shape of the reservoir corresponds to part of a sphere.

8. The phantom of claim 1, wherein at least one of the first or second components comprises a plurality of elongate members, the plurality of elongate members each including an end that has a respective portion of the corresponding first or second outer shape defining part of a respective pocket corresponding to that end, wherein the plurality of elongate members correspond to a plurality of pockets.

9. The phantom of claim 8, wherein the plurality of pockets are arranged in a regular geometric shape.

10. The phantom of claim 9, wherein the regular geometric shape comprises at least one of a ring or a spiral.

11. The phantom of claim 8, wherein the shape of the reservoir comprises portions which locate respective centers of the plurality of pockets.

12. The phantom of claim 1, wherein the first and second components each comprise a reservoir.

13. The phantom of claim 1, wherein at least one of the first or second component comprises at least one elongate member, an end of which comprises the portion of the corresponding first or second outer shape defining the corresponding part of the at least one pocket.

14. The phantom of claim 13, wherein the at least one elongate member is hollow, and wherein the reservoir extends within the elongate member.

15. The phantom of claim 13, wherein the first and second components each comprise at least one elongate member.

16. The phantom of claim 15, wherein the first and second components each comprise a plurality of elongate members.

17. The phantom of claim 1, wherein the first and second components comprise moulded plastic.

18. A kit of parts for forming a phantom for calibration of a medical imaging system, the kit comprising:
a first component having a first outer shape, a portion of which defines part of at least one pocket; and
a second component for coupling to the first component and having a second outer shape, a portion of which defines another part of the at least one pocket when the first and second components are coupled to each other;
wherein at least one of the first or second component comprises a reservoir, the reservoir having a shape at least a portion of which locates a center of the at least one pocket when the first and second components are coupled to each other.

\* \* \* \* \*